United States Patent
Dohlman

(10) Patent No.: US 7,186,233 B2
(45) Date of Patent: Mar. 6, 2007

(54) DRY EYE TREATMENT

(75) Inventor: Claes H. Dohlman, Weston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 11/104,950

(22) Filed: Apr. 13, 2005

(65) Prior Publication Data

US 2005/0240142 A1 Oct. 27, 2005

Related U.S. Application Data

(60) Provisional application No. 60/626,190, filed on Nov. 9, 2004, provisional application No. 60/565,009, filed on Apr. 23, 2004.

(51) Int. Cl.
*A61M 5/00* (2006.01)
*A61B 19/00* (2006.01)

(52) U.S. Cl. ............... 604/8; 604/9; 128/898

(58) Field of Classification Search ........... 604/8, 604/9, 19, 27, 28, 30, 31, 48, 521, 505, 500, 604/502, 264, 523, 93.01, 164.01, 167.03; 606/1, 107–108; 128/897–898, 912; 623/11.11, 623/23.64, 23.68; 138/118
See application file for complete search history.

(56) References Cited

U.S. PATENT DOCUMENTS

| | | | |
|---|---|---|---|
| 3,949,750 A * | 4/1976 | Freeman | 424/427 |
| 4,554,918 A * | 11/1985 | White | 604/10 |
| 4,781,675 A | 11/1988 | White | |
| 4,915,684 A | 4/1990 | MacKeen et al. | |
| 4,959,048 A | 9/1990 | Seder et al. | |
| 5,283,063 A | 2/1994 | Freeman | |
| 5,346,464 A * | 9/1994 | Camras | 604/9 |
| 5,437,625 A * | 8/1995 | Kurihashi | 604/8 |
| 5,830,171 A * | 11/1998 | Wallace | 604/8 |
| 6,041,785 A | 3/2000 | Webb | |
| 6,083,188 A | 7/2000 | Becker | |
| 6,113,567 A | 9/2000 | Becker | |
| 6,306,114 B1 | 10/2001 | Freeman et al. | |
| 6,508,779 B1 | 1/2003 | Suson | |
| 6,510,600 B2 | 1/2003 | Yaron et al. | |
| 6,544,208 B2 | 4/2003 | Ehtier et al. | |
| 6,589,198 B1 | 7/2003 | Soltanpour et al. | |
| 6,682,500 B2 | 1/2004 | Soltanpour et al. | |
| 6,726,676 B2 | 4/2004 | Stegman et al. | |
| 2004/0254516 A1* | 12/2004 | Murray et al. | 604/8 |
| 2005/0119737 A1* | 6/2005 | Bene et al. | 623/4.1 |

\* cited by examiner

*Primary Examiner*—Patricia Bianco
(74) *Attorney, Agent, or Firm*—Fish & Richardson P.C.

(57) ABSTRACT

A dry-eye treatment method includes collecting fluid from the inside of the eye and transporting the collected fluid into the eyelid fornix, where it accumulates. At each blink, accumulated fluid from the fornix is spread across the surface of the eye.

14 Claims, 2 Drawing Sheets

DRY EYE TREATMENT

RELATED APPLICATIONS

This application claims priority under 35 U.S.C. §119 to the U.S. Provisional Patent Applications 60/565,009, filed Apr. 23, 2004 and 60/626,190, filed Nov. 9, 2004.

FIELD OF INVENTION

The invention relates to treatment of dry eye syndrome.

BACKGROUND

The surface of the eye is constantly bathed in tears. Without this coating of tears, the eye would dry out and vision would decrease drastically. An insufficient supply of tears results in a condition known as "dry-eye syndrome."

A variety of treatments are available for dry-eye syndrome. The particular treatment to be used in any one case is selected on the basis of the specific etiology.

One such treatment involves the application of eye drops to provide temporary relief of dry-eye syndrome. In most cases, eye drops are periodically reapplied. This can be inconvenient, particularly if the need to reapply eye drops occurs too frequently. In addition, many patients are uncomfortable with maneuvering a dropper close to the surface of the eye and keeping the eyes open to allow the eye drop to reach the surface of the eye. In severely dry eyes, even application of drops is ineffectual.

SUMMARY

A method for treating severely dry-eye syndrome includes draining fluid from inside the eye into the fornix of the eye at a rate selected such that, with each blink, fluid accumulated in the fornix is spread over the eye.

A method for treating dry-eye syndrome includes collecting fluid from inside the eye; and transporting the collected fluid into the fornix of the eyelid.

In some practices of the invention, transporting the collected fluid includes transporting the fluid at a rate selected such that, with each blink, fluid accumulated in the fornix is spread over the eye.

In other practices of the invention, collecting fluid includes collecting fluid from the interior of the eye. For example, fluid can be collected from the anterior chamber of the eye.

Practices of the invention also include those in which wherein collecting fluid includes inserting a first end of a tube into the anterior chamber of the eye. Optionally, a jacket defining a cavity is placed on the surface of the eye, and a second end of the tube is placed in fluid communication with the cavity.

In those practices in which a tube is used to collect fluid from inside the eye, a pressure-relief valve can be provided at any place between the two ends of the tube or at the ends themselves. Optionally, a pressure threshold associated with the pressure-relief valve can be set on the basis of a fluid pressure in the anterior chamber. In yet another optional practice of the invention, the pressure-relief valve is enclosed in a jacket.

In another aspect, the invention includes a method for treating dry-eye syndrome, by causing the eye to be bathed by fluid produced within the eye.

In some practices, causing the eye to be bathed includes transporting fluid produced within the eye from inside the eye to outside the eye.

Other practices further include causing the transported fluid to accumulate at a location outside the eye. One location that can be used is the fornix.

In another aspect, the invention includes an apparatus for treating dry-eye syndrome. Such an apparatus includes means for extracting fluid from inside the eye; and means for directing the fluid to accumulate at a location outside the eye.

In some embodiments, the means for extracting fluid includes a tube having a first end for insertion inside the eye, and a second end for remaining outside the eye; and a pressure-relief valve coupled to the second end. Optionally, a jacket can enclose the pressure relief valve.

In other embodiments, the means for directing fluid includes a tube configured to direct fluid to the fornix of the eye.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

These and other features and advantages of the invention will be apparent from the following detailed description and the accompanying figures, in which:

DETAILED DESCRIPTION

Figure 1:
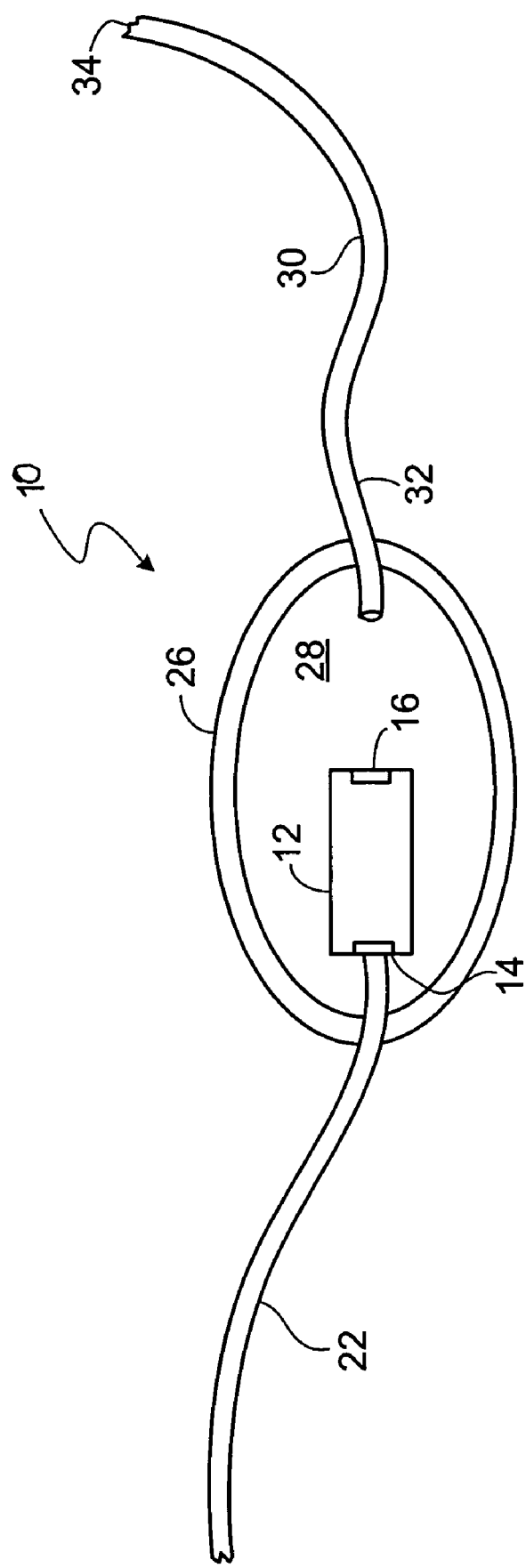
FIG. 1 is a jacketed shunt with a drainage duct.
Figure 2:
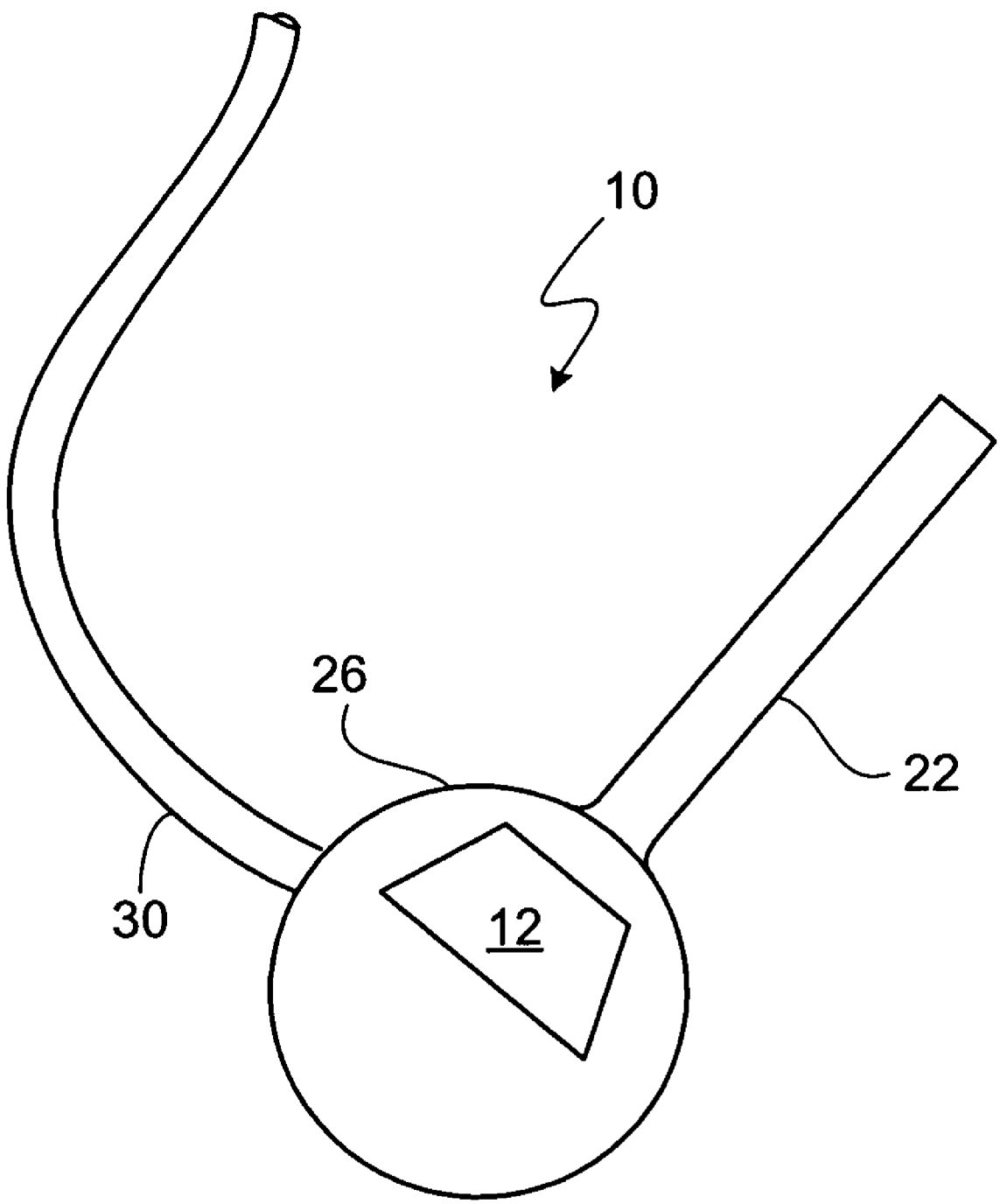
FIG. 2 is a jacketed shunt with a drainage duct for drainage into the fornix behind the lower lid of the eye.

A shunt 10 for treatment of dry eye syndrome, shown in FIG. 1, includes a valve 12 having a valve inlet 14 and a valve outlet 16. The valve 12 is a pressure-regulating valve that opens its outlet 16 whenever the fluid pressure at its inlet 14 is in excess of a pre-determined threshold. An exemplary valve 12 of this type is the Ahmed valve, which is manufactured by New World Medical, Inc. of Rancho Cucamonga, Calif.

A silicone rubber jacket 26 encloses the valve 12 so that fluid from the outlet 16 collects in a cavity 28 defined by the jacket 26. Materials other than silicone rubber can be used to form a jacket 26 around the valve 12. Preferably the jacket material is biocompatible and/or impervious to water.

To provide drainage for the cavity, the shunt 10 includes a drainage duct 30 having a proximal end 32 and a distal end 34. The proximal end 32 of the drainage duct 30 is placed in fluid communication with the cavity 28. The distal end 34 is inserted into fornix of the lower eyelid.

In operation, the jacket 26 is implanted onto the surface of the sclera of the eye. An open proximal end of the intake duct 22 is inserted into the anterior chamber of the eye. Fluid, under pressure, fills the intake duct 22. When the pressure exceeds the pre-defined threshold, the valve outlet 16 opens. This causes the fluid to pass out of the valve 12 and into the cavity 28. This fluid eventually accumulates in the fornix.

For treatment of dry eye syndrome, the pre-defined threshold for opening the value outlet 16 is set so that normal pressure is sufficient to open the valve and pass fluid into the drainage shunt 30 that drains into the fornix. This results in an accumulation of fluid in the fornix. Each time the patient blinks, the fluid collected in the fornix is spread over the surface of the eye, thereby relieving dry-eye syndrome.

The pressure threshold is selected such that fluid drains into the fornix quickly enough to accumulate into a pool having sufficient volume to be spread across the eye surface, but not so fast as to overflow the fornix or to drain the anterior chamber.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Having described the invention, and a preferred embodiment thereof, what I claim as new, and secured by Letters Patent is:

1. A method for treating dry-eye syndrome, the method comprising:
   identifying a patient having an eye afflicted with dry-eye syndrome;
   collecting fluid from inside the afflicted eye; and
   transporting the collected fluid into the fornix of an eyelid.

2. The method of claim 1, wherein collecting fluid comprises collecting fluid from the interior of the eye.

3. The method of claim 2, wherein collecting fluid comprises collecting fluid from the anterior chamber of the eye.

4. The method of claim 3, wherein collecting fluid comprises inserting a first end of a tube into the anterior chamber of the eye.

5. The method of claim 4, wherein collecting fluid comprises placing a jacket defining a cavity on the surface of the eye, and placing a second end of the tube in fluid communication with the cavity.

6. The method of claim 5, further comprising providing a pressure-relief valve in fluid communication with the tube.

7. The method of claim 6, further comprising selecting a pressure threshold associated with the pressure-relief valve on the basis of a fluid pressure in the anterior chamber.

8. The method of claim 5, further comprising enclosing a pressure-relief valve in the jacket.

9. The method of claim 1, wherein transporting the collected fluid comprises transporting the fluid at a rate selected such that, with each blink, fluid accumulated in the fornix is spread over the eye.

10. A method for treating dry-eye syndrome, the method comprising identifying a patient having an eye afflicted with dry-eye syndrome; and causing the afflicted eye to be bathed by fluid produced within the eye.

11. The method of claim 10, wherein causing the eye to be bathed comprises transporting fluid produced within the eye from inside the eye to outside the eye.

12. The method of claim 11, further comprising causing fluid transported from inside the eye to outside the eye to accumulate at a location outside the eye.

13. The method of claim 12, further comprising selecting the location to be the fornix.

14. A method for treating dry-eye syndrome, the method comprising:
   inserting a first end of a tube into an anterior chamber of the eye to collect fluid therefrom;
   placing a jacket on the surface of the eye, the jacket enclosing a pressure-relief valve; placing a second end of the tube in fluid communication with the pressure relief valve;
   transporting the collected fluid through the tube into the fornix of an eyelid.

* * * * *